United States Patent [19]

Leaseburge et al.

[11] Patent Number: 4,684,465
[45] Date of Patent: Aug. 4, 1987

[54] SUPERCRITICAL FLUID CHROMATOGRAPH WITH PNEUMATICALLY CONTROLLED PUMP

[75] Inventors: Emory J. Leaseburge; Thomas J. Thomas, both of Lewisburg, W. Va.

[73] Assignee: Combustion Engineering, Inc., Windsor, Conn.

[21] Appl. No.: 917,466

[22] Filed: Oct. 10, 1986

[51] Int. Cl.⁴ .................................. B01D 15/08
[52] U.S. Cl. ........................ 210/198.2; 55/386; 210/101; 210/136; 417/46; 417/401
[58] Field of Search ............... 210/101, 136, 198.2, 210/656, 659; 73/61.1 C; 417/46, 401; 55/386

[56] References Cited

U.S. PATENT DOCUMENTS

| | | | |
|---|---|---|---|
| 3,362,618 | 1/1968 | Fortinov | 417/401 |
| 3,839,863 | 10/1974 | Frazier | 417/401 |
| 3,963,383 | 6/1976 | Hill | 417/401 |
| 4,128,476 | 12/1978 | Rock | 210/198.2 |
| 4,347,131 | 8/1982 | Brownlee | 210/198.2 |
| 4,368,008 | 1/1983 | Budzich | 417/46 |
| 4,422,942 | 12/1983 | Allington | 210/101 |
| 4,478,720 | 10/1984 | Perrut | 210/198.2 |
| 4,487,080 | 12/1984 | Leaseburge | 73/863.83 |
| 4,580,759 | 4/1986 | Leaseburge | 137/625.48 |
| 4,592,842 | 6/1986 | Tomlinson | 210/198.2 |

*Primary Examiner*—Ernest G. Therkorn
*Attorney, Agent, or Firm*—William W. Habelt

[57] ABSTRACT

An apparatus for analyzing a process stream (1) via supercritical fluid chromatography including container means (10), extraction means (50) for drawing a sample volume from the process stream and injecting the sample volume into the supercritical fluid to form a dilute mix (5), analyzer means (70) for analyzing the dilute mix via supercritical fluid chromatography, sample inlet valve means (60) for receiving the dilute mix from the extraction means (50) and supplying a portion of the dilute mix to the analyzer means (70), pneumatically driven piston-type pump means (30) for drawing the substance from the container means (10) and delivering same under pressure either to the extraction means (50) or to the analyzer means (70) as desired, and control means (40) for supplying low pressure air to the pump means (30) in a controlled manner so as to draw the substance from the container means (10) and maintain the substance at a desired pressure above the supercritical pressure for delivery to the analyzer means (70) and the extraction means (50) as desired.

1 Claim, 2 Drawing Figures

SUPERCRITICAL FLUID CHROMATOGRAPH WITH PNEUMATICALLY CONTROLLED PUMP

BACKGROUND OF THE INVENTION

The present invention relates to supercritical fluid chromatography and, more particularly, to an apparatus for analyzing a process stream via supercritical fluid chromatography having improved pump means for drawing a substance from a container means and delivering a pressurized substance to the analyzing system.

Supercritical fluid chromatography is an analytical technology which permits the analysis of high molecular weight samples in a rapid and efficient manner. The supercritical state is the region above a substance's critical point, which is defined as the temperature and pressure at which the liquid and vapor phases of the substance exists in equilibrium with each other and become identical, forming a single phase. Above this critical point in temperature and pressure, the fluid has a viscosity close to that of a gas but the solubility of a liquid and therefore is uniquely suitable as a mobile phase for transporting a high molecular weight compound through very small diameter tubes and conduits in an analyzer such as a chromatograph. There are several substances which are well known as potential supercritical fluid phases including ammonia, pentane, isobutane, and carbon dioxide.

A supercritical fluid is commonly obtained by pressurizing and heating a substance above its critical temperature and pressure. Once in this supercritical state, a substance will not become a liquid no matter how much pressure is applied. It is necessary to provide pumping means for the pressure to convert a substance to a supercritical fluid. Heretofore, such pumping means have been complicated and cumbersome and have restricted the use of supercritical fluid chromatography in on-line process analysis.

SUMMARY OF THE INVENTION

It is an object of the present invention to provide an apparatus for analyzing a process stream via supercritical fluid chromatography having improved pump means which permits the use of low pressure air for providing the substance in a pressurized state during transfer.

It is the further object of the present invention to provide pumping means having control means permitting low pressure air to be supplied in a controlled manner so as to deliver a pressurized substance to the analyzer at a desired pressure.

The apparatus of the present invention for analyzing a process stream via supercritical fluid chromatography comprises container means for storing a substance, extraction means for drawing a sample volume from the process stream and injecting the sample volume into the supercritical fluid to form a dilute mix, analyzer means for analyzing the dilute mix via supercritical fluid chromatography, sample inlet valve means for receiving the dilute mix from the extraction means and supplying a portion of the dilute mix to the analyzer means, pump means for drawing the substance from the container means and delivering same either to the extraction means or to the analyzer means as desired, and means for supplying low pressure air to the pump means in a controlled manner so as to draw the substance from the container means and maintain the the substance at a desired pressure above the critical pressure for delivery to the analyzer means and the extraction means as desired.

The pump means of the present invention comprises a pneumatically driven piston-type pump having a first large diameter chamber, a second small diameter chamber extending axially therefrom, and an axially extending piston rod enclosed therebetween. The piston rod has a first large diameter head disposed and axially translatable in sealing relationship within the first chamber and a second small diameter head disposed and axially translatable in sealing relationship within the second chamber. The control means supplies low pressure air to the first chamber of the pump means in a controlled manner so as to draw the substance from the container means into the second chamber of the pump means when the pressurized air is vented from the first chamber and to compress the substance drawn into the second chamber to maintain the substance at a desired pressure above the critical pressure.

Preferably, the control means comprises in combination transducer means for monitoring the pressure of the pressurized substance within the second chamber of the pump means, proportioning control valve means for controlling the amount of air flow supplied to the first chamber of the pump means to act upon the piston rod for compressing the substance confined within the second chamber of the pump means, and programmable controller means, preferably a microprocessor, connected to receive a signal from the transducer means indicative of the pressure within the second chamber of the pump means and, in response thereto, transmit a control signal to the proportioning control valve so as to regulate the valve to control the amount of air flow therethrough to provide the desired pressure within the second chamber of the pump means by controlling the pressure of the air supply within the first chamber of the pump means.

BRIEF DESCRIPTION OF THE DRAWING

The present invention will be described hereinafter with reference to the accompanying drawing wherein.

DETAILED DESCRIPTION OF A PREFERRED EMBODIMENT

Figure 1:
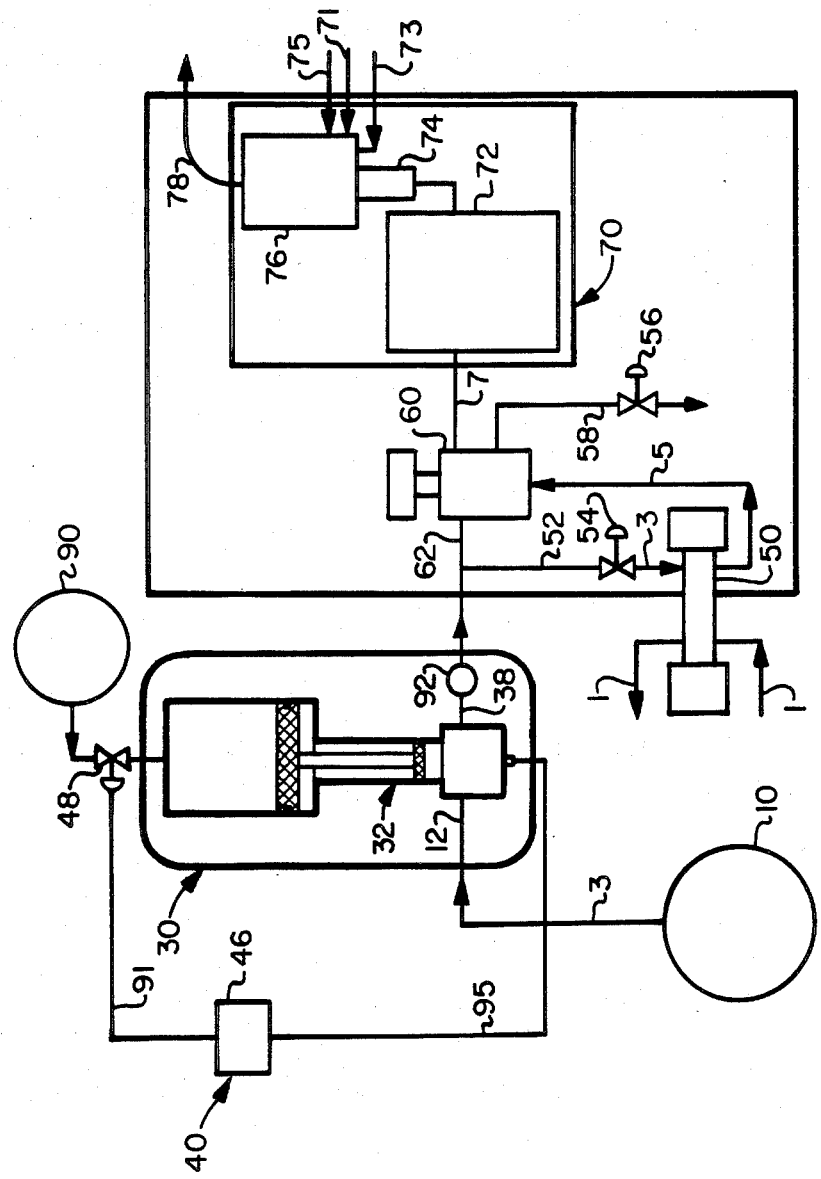
FIG. 1 is a schematic representation of a preferred embodiment of the apparatus of the present invention.

Referring now to FIG. 1, there is schematically depicted therein an apparatus for analyzing a process stream via supercritical fluid chromatography embodying the present invention. The primary components making up the apparatus of the present invention are container means 10 for storing a substance, a supercritical fluid chromatograph 20 wherein the sample is prepared and analyzed, pump means 30 interconnected therebetween for drawing the substance from the container means 10 and delivering the pressurized substance to the chromatograph 20, and control means 40 for controlling the supply of low pressure air to the pump means.

In the best mode embodiment of the invention presently contemplated, the chromatograph 20 includes extraction means 50, sample inlet valve 60, and analyzer means 70. In operation, extractor means 50 is activated to draw a sample volume from the process stream 1 and inject the sample volume into a stream of supercritical fluid 3 whereby the sample volume is diffused into the supercritical fluid to form a dilute mix 5 which is transferred to the sample inlet valve 60. A typical sample withdrawn from the process stream 1 via the extraction means 50 would have a volume of 1 microliter and would be introduced within the extraction means into a stream of supercritical fluid to produce a dilute mix of the sample volume diffused within the supercritical fluid. The supercritical fluid is supplied to the extractor means 50 through delivery line 52 by opening valve 54 as desired.

The dilute mix of the sample from the process stream 1 diffused in the supercritical fluid 3 passes from the extractor means 50 to sample inlet valve 60. The dilute mix passes through the sample inlet valve 60 and a fixed volume of sample is passed to the analyzer means 70 to be analyzed via supercritical fluid chromatography.

The analyzer means 70 may constitute any of a number of known commercially available apparatus or the like for analyzing a sample by supercritical fluid chromatography. Although the exact composition of the analyzer means 70 is not critical to the present invention, it is presently contemplated that analyzer means 70 would include, as shown in the drawing, a column oven 72, a flame ionization detector 76 disposed downstream of the column oven 72 and interconnected therewith through interface means 74 to receive dilute mix sample to be analyzed from the column oven 72. The column oven 72 may be any suitable commercially available oven capable of heating the column which receives the dilute mixture from the sample inlet valve 60 to the temperature required for proper chromotographic separation.

Although a number of detectors could be utilized as the detector means 76, such as ultraviolet detectors, or infrared detectors, it is presently contemplated that detector means 76 comprise a flame ionization detector. The flame ionization detector 76 is of conventional design and is maintained a temperature above 300° C. to prevent the sample from condensing at the ambient pressure existing in the detector. Hydrogen gas 71 and nitrogen gas 73 are supplied to the flame ionization detector as fuel and dilution gas, respectively, together with combustion air 75 to produce a flame within the detector into which the dilute mix sample is passed through interface means 74 so that the species within the sample may be ionized for detection in accordance with conventional flame ionization detection techniques. The combustion products from the flame ionization detector are vented from the chromatograph 20 through vent line 78.

Interface means 74 is provided for delivery of the dilute mix from the column oven 72 into the detection means 74. The dilute mix of process sample dissolved in supercritical fluid exits the column located in the oven 72 at a pressure of about 7000 psi to pass into the ionization detector 76 which is maintained at ambient pressure conditions. The interface means 74 serves to dissipate the energy liberated during this transition from very high pressure to ambient pressure.

Figure 2:
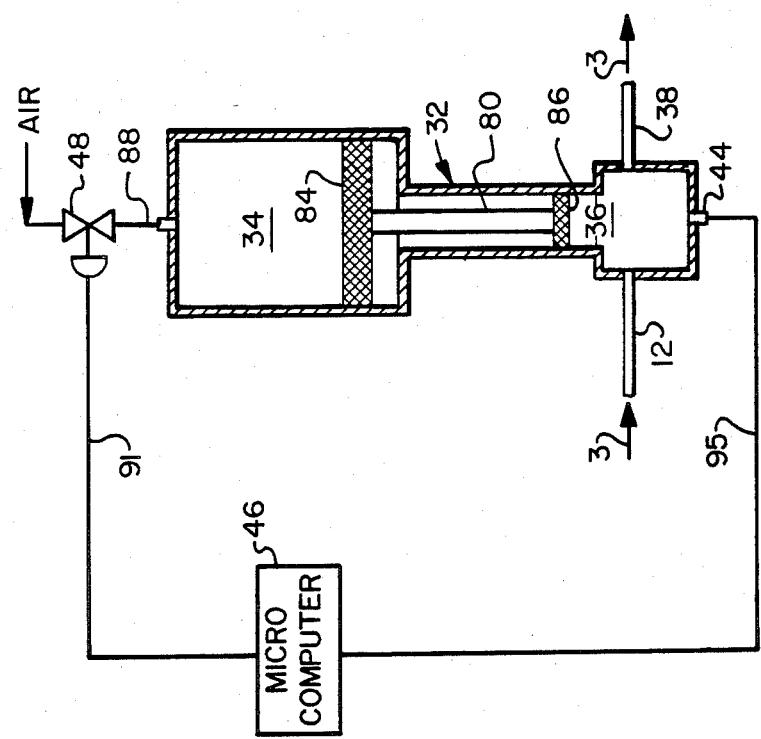
FIG. 2 is an enlarged schematic view of the pump employed in the apparatus of FIG. 1.

As best seen in FIG. 2, the pump means 30 for receiving the substance from the container means 10 through supply line 12 and delivering the pressurized substance either to the extraction means 50 through a first delivery line 52 or to the sample inlet valve 60 through a second delivery line 62 comprises a pneumatically driven piston-type pump 32 having a first larger diameter chamber 34, a second smaller diameter chamber 36 extending axially from the larger diameter chamber 34, and an axially extended piston rod 80 enclosed and extending therebetween. The piston rod 80 has a first large diameter head 84 disposed and axially translatable in sealing relationship within the first chamber 34 and a second small diameter head 86 disposed and axially translatable in sealing relationship within the second chamber 36.

In operation, pressurized air from air supply 90, typically at a pressure of about 80 psi, is passed through control valve 48 and conduit 88 to the first larger diameter chamber 34 of the pump 32 to generate a force against the large diameter piston head 84 thereby causing the piston rod 80 to translate axially within the pump 34 thereby compressing the substance within the second smaller diameter chamber 36 of the pump 32 by movement of the small diameter head 86 on the opposite end of the piston rod 80. In this manner, the substance may be compressed to and maintained at a desired pressure which is above that substance's critical pressure. It can be supplied to the chromatograph 20 through outlet line 38 and filter 92 at desired rates. When the analysis is complete, the system is depressurized by venting the air from the first larger diameter chamber 34 of the pump means 80 thereby resulting in the piston rod 80 withdrawing axially from the second smaller diameter chamber 36 further into the larger diameter chamber 34 and simultaneously drawing additional chemical substance, such as carbon dioxide, from the container means 10 through line 12 to refill chamber 36.

In order to facilitate supply of supercritical fluid to the chromatograph 20 at desired pressures, control means 40 is provided which comprises pressure transducer means 44 operatively associated with pump 32 to sense the pressure existing in the smaller diameter chamber 36 of the pump 32, a microprocessor 46, preferably programmable, adapted to receive a signal 95 from the pressure transducer 44, and flow control valve 48 disposed in the air supply conduit 88 for controlling the flow of air therethrough from air supply 90 in response to the signal 91 received from the microprocessor 46. The pressure transducer means 44 is mounted in the wall of the smaller diameter chamber 36 of the pump 32 to sense the pressure therein and send a continuous signal 95 indicative of the pressure within the chamber 36 to the microprocessor 46.

The microprocessor 46 processes the signal 95 and generates a signal 91 which is sent to flow control valve 48 to manipulate the control valve to increase or decrease the flow of pressurized air from the air supply 90 through the conduit 88 to the larger diameter chamber 34 of the pump 32 as a means of controlling the force exerted by the air pressure upon the piston head 84 within the larger diameter chamber 34 and therefore control the compression force exerted upon the substance within the smaller diameter chamber 36 at the opposite end of the pump 32. The microprocessor 46 is preferably programmable so that the operator may input any desired pressure and flow rate at the control conditions against which the microprocessor 46 will process the pressure signal 95 received from the transducer means 44 and generate the control signal 91. The microprocessor can also be programmed to provide changes in the pressure in the chamber 36 over the period of analysis and time the venting and pressuring of the larger diameter chamber 34 so as to control the refilling and compressing of the substance in the smaller diameter chamber 36 and activate the supply of pressurized substance to the chromatograph 20.

Accordingly, the present invention provides a pump which is capable of rapid cycling so that numerous analysis can be conducted in repeating fashion as the pump may be refilled with substance simply by relieving the air pressure within the larger diameter chamber 34 driving the piston rod 80 by venting the air therefrom and simultaneously drawing substance into the smaller diameter chamber at the opposite end of the pump 32.

Additionally, as the pump of the present invention is strictly pneumatically operated, this pump can be used in hazardous areas wherein motor-driven pumps cannot be used due to fear of electrical arcing which would result in a spark which could cause explosions in hazardous areas. Further, due to the few moving parts involved, the pump of the present invention inherently requires less maintenance than motor-driven pumps which have numerous moving parts involved in their gear trains.

We claim:

1. An apparatus for analyzing a process stream via supercritical fluid chromatography comprising:
   a. chromatograph means for analyzing a sample of the process stream diluted in a volume of the supercritical fluid via supercritical fluid chromatography;
   b. pump means for drawing a supercritical fluid substance from a supply means through a supply line, pressurizing said supercritical fluid substance and delivering said pressurized supercritical fluid substance to said chromatograph means, said pump means comprising a pneumatically driven piston type pump having a first large diameter chamber, a second smaller diameter chamber extending axially therefrom, and an axially extending piston rod having a first large diameter head disposed and axially translatable in sealing relationship within the first chamber and a second smaller diameter head disposed and axially translatable in sealing relationship within the second chamber; and
   c. control means for controlling the supply low pressure air to the first chamber of said pump means in a controlled manner so as to draw said supercritical fluid substance from said container means into the second chamber when the pressurized air is vented from the first chamber and to compress said substance drawn into the second chamber to maintain said supercritical fluid substance at a desired pressure above the critical pressure for delivery to said chromatograph means.

* * * * *